United States Patent [19]

Niwano et al.

[11] Patent Number: 5,418,251

[45] Date of Patent: May 23, 1995

[54] TOPICAL COMPOSITION FOR ACCELERATING WOUND HEALING

[75] Inventors: Yoshimi Niwano, Osakasayama; Hiroyasu Koga, Kawachinagano; Masahiro Hayashi; Kazuo Kanai, both of Sakai, all of Japan

[73] Assignee: Nihon Nohyaku Co., Ltd., Japan

[21] Appl. No.: 313,609

[22] Filed: Sep. 29, 1994

Related U.S. Application Data

[63] Continuation of Ser. No. 4,238, Jan. 14, 1993, abandoned.

[30] Foreign Application Priority Data

Jan. 17, 1992 [JP] Japan .................................. 4-027143

[51] Int. Cl.$^6$ ........................................... A61K 31/385
[52] U.S. Cl. ..................................................... 514/440
[58] Field of Search ......................................... 514/440

[56] References Cited

U.S. PATENT DOCUMENTS

4,118,506 10/1978 Taninaka et al. .................... 424/277

FOREIGN PATENT DOCUMENTS

2188842 10/1987 United Kingdom .

OTHER PUBLICATIONS

Chemical Abstracts 98: 46622f (1983).
Chemical Abstracts, vol. 98, No. 7 Columbus, Ohio, US; abstract No. 46622f, Shows Igakkai Zasshi, vol. 42, No. 3 1982, pp. 293–300 M. Kano et al. "The Antiinflammatory, Wound Healing and Membrane-stabilizing effects of Diisopropyl 1–3–dithiol–2–ylidenemalonate (malotilate)".
Patent Abstracts of Japan, vol. 009, No. 233 (C–304), Sep. 19, 1985 & JP–A–60 092 216 (Nihon Noyaku KK) 23 May 1985.
Database WPIL, Week 8410, Derwent Publications Ltd., London, GB; AN 84–059246 & JP–A–59 016 819 (Nihon Noyaku KK) Jan. 28, 1984.
Patent Abstracts of Japan, vol. 6, No. 122 (C–112), Jul. 7, 1982.
English Translation of Journal of Showa Medical Association, Kano et al., vol. 42, No. 3, pp. 293–300 (1982).

*Primary Examiner*—Raymond Henley, III
*Assistant Examiner*—Phyllis G. Spivack
*Attorney, Agent, or Firm*—Cushman Darby & Cushman

[57] ABSTRACT

Topical compositions are disclosed that comprise a compound represented by formula (I)

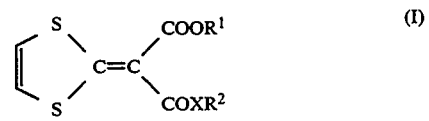

wherein $R^1$, $R^2$ and X are as defined in the specification as an effective ingredient that are effective for accelerating wound healing.

6 Claims, No Drawings

TOPICAL COMPOSITION FOR ACCELERATING WOUND HEALING

This is a continuation of application Ser. No. 08/004,238, filed on Jan. 14, 1993, now abandoned.

BACKGROUND OF THE INVENTION

1. Field of the Invention

The present invention relates to a composition for accelerating wound healing comprising as an effective ingredient a compound represented by general formula (I):

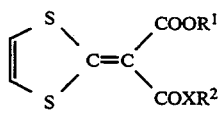

wherein $R^1$ represents an alkyl group having 1 to 6 carbon atoms; $R^2$ represents an alkyl group having 1 to 10 carbon atoms, an alkenyl group having 2 to 6 carbon atoms or a cycloalkyl group having 3 to 7 carbon atoms; and X represents —O— or —NH—.

2. Related Art

Wounds are damages of surface tissues caused by surgical incision; gastrointestinal wounds or ulcer, burn induced by heat; UV rays or chemicals, ablation, lacerated wounds, amputation, wounds by pressure called "bedsore" or decubitus, erosion, etc. and infections. Particularly in patients who will receive surgical operation, their physical capability is generally declined seriously an most cases. It is thus desired to accelerate healing positively and directly, without relying only on natural healing of wounds. Turning to a bedsore, not only a patient himself suffers from pain but huge costs are required for healing such wounds. This appears to be a serious social problem as aged people increase. Healing of these wounds depends generally on the formation of new connective tissue and epithelial tissue due to cell growth and drugs that stimulate or promote the course of cell differentiation or cell growth included in the progress of healing wounds are considered to be very effective for the treatment.

As those showing an activity of promoting wound healing, there are known, as the effective ingredient, the extract of aloe, antibiotics, anti-inflammatory agents, kallikrein, adenine, nicotinic acid, allantoin, vitamin A, zinc, c-AMP derivatives (Japanese Patent Application KOKAI No. 107935/1988), exogenous DNA (Japanese Patent Application KOKAI No. 505888/1988), etc. The main trend was to improve pharmaceutical preparations in order to improve absorbability of these drugs as the effective ingredient. As various findings on dermatohistology were recently revealed, an attempt to use epithelial growth factor (b-EGF) for post-operative wound healing has also been reported (Japanese Patent Application KOKAI No. 106823/1991).

However, only a part of chemicals is effective in wound site by oral administration so that the effect is exhibited only with difficulty. In addition, there is a concern that Side effects might be caused. Accordingly, it is desired to use drugs for treatment which directly act on the skin topically to heal wounds. However, a few drugs for wound healing are known for topical use and make it difficult to heal wounds on the skin.

In general formula (I), compounds wherein $R^1$ and $R^2$ are isopropyl and X is oxygen are known to show action for accelerating wound healing when these compounds are orally administered [Journal of Showa Medical Association, vol. 42 No. 3, 293–300 (1982)]. However, the effect is equal to that of commercially available Solcoseryl in a dose of 1000 times that of Solcoseryl, meaning that the effect is far from its practical level. Taking it into account, the drug was not expected to be used for topical application.

OBJECT AND SUMMARY OF THE INVENTION

Under the actual situation, the present inventors have made investigations on various drugs for external use with respect to their wound healing effect. It has thus been found that the compounds represented by general formula (I) exhibits the wound healing effect equivalent to or superior to commercially available Solcoseryl, when applied externally, in a dose of 3/50 to 1/5 times that of Solcoseryl and the effect is quite unexpected from the effect when orally administered. The present invention has thus been completed.

The present invention is concerned with a composition for accelerating wound healing comprising as an effective ingredient a compound represented by general formula (I):

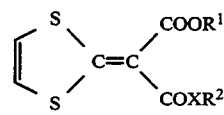

wherein $R^1$ represents an alkyl group having 1 to 6 carbon atoms; $R^2$ represents an alkyl group having 1 to 10 carbon atoms, an alkenyl group having 1 to 6 carbon atoms or a cycloalkyl group having 3 to 7 carbon atoms; and X represents —O— or —NH—.

DETAILED DESCRIPTION OF PREFERRED EMBODIMENTS

In the general formula (I), examples of an alkyl group having 1 to 6 carbon atoms include methyl, ethyl, n-propyl, i-propyl, n-butyl, i-butyl, n-pentyl, n-hexyl, etc.; examples of an alkyl group having 1 to 10 carbon atoms include methyl ethyl, n-propyl, i-propyl, n-butyl, i-butyl, n-pentyl, n-hexyl, n-heptyl, n-octyl, n-decyl, etc.; example of an alkenyl group having 2 to 6 carbon atoms include vinyl, allyl, 1-butenyl, 1-pentenyl, 1-hexenyl etc.; and examples of a cycloalkyl group having 3 to 7 carbon atoms include cyclopropyl, cyclopentyl, cyclohexyl, cycloheptyl, etc.

Some of the compounds represented by general formula (I) are novel and synthesized in a manner similar to the process described in Japanese Patent Application KOKOKU No. 56708/1980.

Next, representative examples of the compounds used in the present invention are shown in Table 1 but the present invention is not limited thereto.

TABLE 1

| No. | $R^1$ | $XR^2$ | Physical Property |
|---|---|---|---|
| 1 | $CH_3$ | $OCH_3$ | m.p. 125~129° C. |
| 2 | i-$C_3H_7$ | O-i-$C_3H_7$ | m.p. 59~60° C. |
| 3 | i-$C_3H_7$ | O—$C_2H_5$ | m.p. 54° C. |
| 4 | i-$C_3H_7$ | 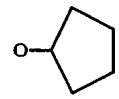 | m.p. 68~69° C. |

TABLE 1-continued

| No. | R¹ | XR² | Physical Property |
|---|---|---|---|
| 5 | i-C₃H₇ | O-n-C₆H₁₃ | m.p. 40° C. |
| 6 | i-C₃H₇ | O—CH₂CH=CH₂ | m.p. 48° C. |
| 7 | i-C₃H₇ | 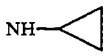 | m.p. 70~72° C. |
| 8 | i-C₃H₇ | NH-n-C₆H₁₃ | $n^{23}_D$ 1.5728 |

Next, synthesis examples of the compounds represented by general formula (I) are shown below.

Synthesis Example 1

Dimethyl 1,3-dithiol-2-ylidenemalonate (Compound No. 1)

After 5.28 g (0.04 mol) of dimethyl malonate and 3.66 g (0.048 mol) of carbon disulfide were dissolved in 25 ml of dimethylsulfoxide, 10.9 g of 45% potassium hydroxide aqueous solution was dropwise added to the solution under ice cooling. The mixture was stirred at room temperature for 20 minutes. The resulting reaction solution was dropwise added to a mixture of 19.6 g of 40% chloroacetaldehyde and 2.88 g of glacial acetic acid below 5° C. The mixture was stirred at the same temperature for 30 minutes. The reaction solution was poured onto ice water. The mixture was extracted twice with ethyl acetate followed by washing with water. After drying over magnesium sulfate, the solvent was distilled off under reduced pressure to give dimethyl 3-hydroxy-1,3-dithiol-2-ylidenemalonate. The thus obtained compound and 12.2 g (0.12 mol) of triethylamine were dissolved in 20 ml of dioxan and 6.9 g (0.06 mol) of methanesulfonyl chloride was slowly added dropwise to the solution. After completion of the dropwise addition, the mixture was stirred at room temperature for 10 minutes and then heated to reflux for 10 minutes. The solution was poured into ice water and the mixture was extracted with ethyl acetate. After drying over magnesium sulfate, the solvent was distilled off under reduced pressure. The residue was purified by silica gel column chromatography (n-hexane: ethyl acetate=2:1) to give 4.0 g (yield 43%) of crystals showing a melting point of 125° to 129° C.

Synthesis Example 2

Compound No. 2 was obtained in a manner similar to Synthesis Example 1.

Synthesis Example 3

Ethyl isopropyl 1,3-dithiol-2-ylidenemalonate (Compound No. 3).

After 14.4 g (0.05 mol) of diisopropyl 1,3-dithiol-2-ylidenemalonate was dissolved in 50 ml of isopropanol, 2.95 g (0.074 mol) of sodium hydroxide aqueous solution was dropwise added to the solution at 30° C. The mixture was stirred for an hour and the resulting potassium salt was dissolved in 50 ml of water. The solution was acidified with 6N hydrochloric acid and the aqueous phase was extracted with dichloromethane. The organic phase was washed with water. After drying, the organic phase was concentrated under reduced pressure. The precipitated crystals were filtered to give 8.5 g (yield 70%) of isopropyl hydrogen 1,3-dithiol-2-ylidenemalonate as white crystals. Then, 2.7 g (0.011 mol) of the thus obtained crystals, 3.6 g (0.012 mol) of 2-chloro-1-methylpyridium p-toluenesulfonate were dissolved in 20 ml of dichloromethane. To the solution was dropwise added a solution of 0.51 g (0.011 mol) of ethanol and 3.46 g (0.034 mol) of triethylamine at 10° C. The mixture was stirred at room temperature for 2 hours. After the reaction solution was poured onto ice water followed by extraction with dichloromethane. The extract was washed successively with 2N hydrochloric acid, 10% sodium carbonate solution and then water. After drying over magnesium sulfate, the solvent was distilled off under reduced pressure. The residue was purified by silica gel column chromatography (n-hexane: ethyl acetate=2:1) to give 1.0 g (yield 35%) of the objective product. Synthesis Examples 4 to 8

Compound Nos. 4 to 8 were obtained in a manner similar to Synthesis Example 3.

By formulating the compound of the present invention in base for topical use, the composition of the present invention for accelerating wound healing is prepared in various forms suitable for topical application, e.g., emulsion, ointment, cream, lotion, cataplasm, etc. An amount of the compound of the present invention formulated in a base can be appropriately chosen from the range of generally 0.01 to 50%, preferably 0.05 to 10%, more preferably 0.1 to 3%, based on the base.

Next, the present invention is explained with reference to examples but is not limited thereto, wherein parts are by weight otherwise indicated.

EXAMPLE 1

| Compound of this invention | 0.1–3.0 parts |
|---|---|
| Polyethylene glycol 400 | 48.5–49.95 parts |
| Polyethylene glycol 4000 | 48.5–49.95 parts |

After the above components were mixed and melted with heating, the solution was cooled to give ointment.

EXAMPLE 2

| Compound of this invention | 0.1–3.0 parts |
|---|---|
| Stearyl alcohol | 5.0 parts |
| Cetanol | 5.0 parts |
| Medium chain fatty acid triglyceride | 10.0 parts |
| Isopropyl myristate | 5.0 parts |
| Polysorbate 60 | 4.0 parts |
| Sorbitan monostearate | 1.0 part |
| Methyl p-oxybenzoate | 0.14 part |
| Propyl p-oxybenzoate | 0.06 part |
| Dibutylhydroxytoluene | 0.02 part |
| Purified water | balance |

The above components were treated in a conventional manner.

Test Example 1

Rats were clipped on their back, and two circular excisional wounds (1 cm in diameter) per animal were made by cutting out the dorsal skin (from epidermis to subcutaneous tissue). One day after the wound was made, cream preparation of the compound (containing 0.1, 0.3 and 1.0%) of the present invention was applied to the wound in a dose of 60 mg/site/day. For reference, commercially available 5% Solcoseryl ointment (Tobishi Co., Ltd.) was similarly applied. On Days 5, 6 and 7, the wound site was traced and the square measure of the area was calculated with an image analyzer (image processor TVIP-5100, Olympus Optical Co., Ltd.). At the same time, the wound skin was excised for histopathological observation by a light microscope.

The results of determination of the wound area are shown in Table 2. The value is shown in terms of specific area when the wound area is made 100% at the time when the drug began to be applied. On Days 5, 6 and 7 after the onset of application, animal was sacrificed for histopathological inspection so that the number of wounds in each group decreased by 2 each from the next day of sacrifice.

TABLE 2

| Test Group | Specific Area of Wound (%) | | |
|---|---|---|---|
| | Day 5 after the onset of Application | Day 6 after the onset of Application | Day 7 after the onset of Application |
| Non-treated control group | 81 | 73 | 57 |
| Vehicle control group | 76 | 55 | 31 |
| 5.0% Solcoseryl | 67 | 40 | 21 |
| 0.1% Compound No. 2 | 75 | 43 | 23 |
| 0.3% Compound No. 2 | 65 | 34 | 15 |
| 1.0% Compound No. 2 | 62 | 37 | 19 |

As is clearly noted from Table 2, the compound of the present invention accelerated reduction in the wound area in any concentration and the effect was better than Solcoseryl ointment used as a reference drug. Also in the histopathological finding, angiogenesis, epidermal differentiation and keratinization and granulation tissue formation in corium and its organization were accelerated as compared to the control groups.

Test Example 2

Serious skin burns (1.7 cm in diameter each) of grade III were produced in rats by application of the mixture of sodium nitrate and potassium nitrate (7:3) heated at 240° C. on their abdominal skin for 20 seconds. Macrogol ointment of the compound of the present invention (containing 0.1, 0.3 and 1.0%) was consecutively applied to the wound in a dose of 240 mg/site/day from the day when the burn was produced. For reference, Macrogol ointment (containing 3%) of commercially available Dibutyl Cyclic AMP (DBcAMP) was similarly applied. Then, the wound site was traced with the passage of time and the square measure of the area was calculated with an image analyzer (image processor TVIP-5100, Olympus Optical Co., Ltd.). The results are shown in Table 3.

TABLE 3

| Test Group | Specific Area of Wound (%) | | |
|---|---|---|---|
| | Day 7 after the onset of Application | Day 10 after the onset of Application | Day 13 after the onset of Application |
| Non-treated control group | 114 | 102 | 60 |
| Vehicle control group | 107 | 95 | 58 |
| 3.0% DBcAMP | 96 | 83 | 58 |
| 0.1% Compound No. 2 | 92 | 77 | 50 |
| 0.3% Compound No. 2 | 93 | 77 | 50 |
| 1.0% Compound No. 2 | 88 | 78 | 50 |

As is clearly noted from Table 3, the compound of the present invention accelerated reduction in the wound area in any concentration and the effect was better than DBcAMP used as a reference drug.

Test Example 3

Under ether anesthesia rat was shaved and the back skin was excised (to about 2 cm) along the vertebra and one sterilized cotton pellet was implanted subcutaneously under the left and right scapulae. Immediately thereafter the excised site was sutured by surgical instant adhesive. After the operation, a 1:1 mixture of penicillin G (10,000 units/ml) and streptomycin (1 g titer, 8 mg/ml) was intramuscularly administered in a dose of 0.2 ml/rat. For consecutive 7 days from the operation, PEG 400 or 0.5% (w/v) PEG 400 solution of the test compound was subcutaneously administered in a dose of 0.1 ml/site/day to the site in which the cotton pellet was implated. On the next day. (Day 7 after the cotton pellet implantation) after the final administration of the test compound, rat was anesthesized to death with ether and granulation tissue formed around the cotton pellet was removed together with the cotton pellet. The thus obtained granulation tissue was dried in vacuuo at room temperature in the presence of phosphorus pentoxide and the dry weight of granulation with the cotton pellet was measured. The results are shown in Table 4.

TABLE 4

| Test Group | Dry Weight of Cotton Pellet and Granulation (mg) | Average ± Standard Deviation |
|---|---|---|
| Intact group | 105 ± 14 | |
| Base control group | 106 ± 22 | |
| Compound No. 1 | 114 ± 18 | |
| Compound No. 2 | 130 ± 16 | |
| Compound No. 3 | 124 ± 26 | |
| Compound No. 4 | 120 ± 33 | |
| Compound No. 5 | 130 ± 39 | |
| Compound No. 6 | 131 ± 30 | |
| Compound No. 7 | 124 ± 23 | |
| Compound No. 8 | 118 ± 24 | |

As shown in Table 4, the compounds of the present invention significantly increased the dry weight of granulation tissue by the cotton pellet implantation to show an activity of accelerating the formation of granulation tissue.

As is described above, the composition of the present invention for topical application possesses the action of accelerating wound healing in a lower dose than in commercially available drugs for reference, and is effective as the composition for accelerating wound healing.

What is claimed is:

1. A topical composition for accelerating wound healing comprising as an effective ingredient a compound represented by formula (I):

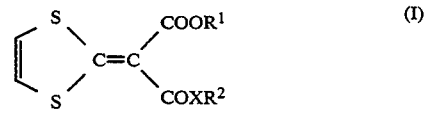

wherein $R^1$ represents an alkyl group having 1 to 6 carbon atoms; $R^2$ represents an alkyl group having 1 to 10 carbon atoms, an alkenyl group having 2 to 6 carbon atoms or a cycloalkyl group having 3 to 7 carbon atoms; and X represents —O— or —NH—.

2. A composition for accelerating wound healing according to claim 1, wherein $R^1$ represents an alkyl group having 1 to 6 carbon atoms; $R^2$ represents an alkyl group having 1 to 10 carbon atoms; and X represents —O— or —NH—.

3. A composition for accelerating wound healing according to claim 1, which is diisopropyl 1,3-dithiol-2-ylidenemalonate.

4. A method for accelerating wound healing which comprises topically applying to the wound and proximity, a therapeutically effective amount of a composition comprising a pharmaceutically acceptable carrier and as an effective ingredient a compound represented by general formula (I):

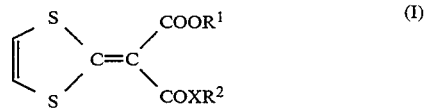

wherein $R^1$ represents an alkyl group having 1 to 6 carbon atoms; $R^2$ represents an alkyl group having 1 to 10 carbon atoms, an alkenyl group having 2 to 6 carbon atoms or a cycloalkyl group having 3 to 7 carbon atoms; and X represents —O— or —NH—.

5. The method of claim 4 wherein $R^1$ represents an alkyl group having 1 to 6 carbon atoms; $R^2$ represents an alkyl group having to 1 to 10 carbon atoms; and X represents —O— or —NH—.

6. The method of claim 4 wherein said compound is diisopropyl 1,3-dithiol-2-ylidenemalonate.

* * * * *